(12) United States Patent
Wei et al.

(10) Patent No.: US 7,508,216 B2
(45) Date of Patent: Mar. 24, 2009

(54) METHOD FOR MEASURING WORK FUNCTION

(75) Inventors: Wei Wei Wei, Beijing (CN); Kai-Li Jiang Jiang, Beijing (CN); Shou-Shan Fan Fan, Beijing (CN)

(73) Assignees: Tsinghua University, Beijing (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 129 days.

(21) Appl. No.: 11/640,056

(22) Filed: Dec. 14, 2006

(65) Prior Publication Data
US 2008/0012587 A1   Jan. 17, 2008

(30) Foreign Application Priority Data
Jul. 14, 2006  (CN) .......................... 2006 1 0061641

(51) Int. Cl.
*G01R 31/26* (2006.01)
(52) U.S. Cl. ..................... 324/467; 324/719; 313/311
(58) Field of Classification Search ................. 324/719, 324/467; 313/311; 427/77; 315/168.3
See application file for complete search history.

(56) References Cited

U.S. PATENT DOCUMENTS

| | | | | |
|---|---|---|---|---|
| 3,394,301 A | * | 7/1968 | Oostrom | 324/467 |
| 5,180,951 A | * | 1/1993 | Dworsky et al. | 315/169.3 |
| 2003/0044519 A1 | * | 3/2003 | Takai | 427/77 |
| 2004/0169453 A1 | * | 9/2004 | Ahn et al. | 313/311 |
| 2005/0276331 A1 | * | 12/2005 | Lee et al. | 375/240.17 |

\* cited by examiner

*Primary Examiner*—Vincent Q Nguyen

(57) ABSTRACT

A method for measuring work function includes the steps of: (a) providing a field emission electron source having a carbon nanotube tip as a cathode electrode and a spaced anode electrode, having a predetermined spaced distance therebetween; (b) applying a voltage between the cathode electrode and the anode electrode and measuring a first current-voltage curve of the field emission electron source in a vacuum environment; (c) forming a layer of field emission material at least on the surface of the carbon nanotube tip; (d) measuring a second current-voltage curve of the now-treated field emission electron source in the same conditions as that in the step (b); (e) achieving two Fowler-Nordheim curves calculated from the two current-voltage curves according to the Fowler-Nordheim equation; and (f) comparing the two Fowler-Nordheim curves and calculating the work function of the field emission material therefrom.

11 Claims, 5 Drawing Sheets

METHOD FOR MEASURING WORK FUNCTION

BACKGROUND

1. Field of the Invention

The invention relates generally to methods for measuring work function and, more particularly, to methods for measuring work function of field emission material.

2. Discussion of Related Art

Work function is the minimum energy needed to remove an electron from a metal to a critical point immediately outside the metallic surface. The work function is an important property of the metal and is usually measured in electron volts. Generally, the measurement for work function of the metal is important for the research of electronic emission properties of the metal. Commonly, the electronic emission of the metal includes thermionic emission and field emission. In the thermionic emission, the electron gains its energy from the heat when the metal is heated to a relatively high temperature. In the field emission, the electron gains its energy from the electric field and is removed from the metallic surface because of an electronic tunneling effect.

A conventional method for measuring work function is adopted in the thermionic emission for measuring the work function of the metal. Specifically, a metal emitter to be measured is provided as a cathode electrode with a spaced anode electrode in a vacuum diode. The metal emitter is heated and an outer electric field is applied between the anode electrode and the cathode electrode. When the metal emitter is heated to a relatively high temperature (about 1000° C.), a plurality of electrons may overcome the work function barrier of the metal emitter and escape outward from the metallic surface. Further, the escaped electrons may be moved from the cathode electrode to the anode electrode. The continual thermionic emission in the electric field will make a continual electric current produced between the two electrodes. Furthermore, the Richardson-Dushman equation relates the current density of a thermionic emission to the work function (W) and temperature (T) of the emitting material is expressed as follows:

$$j_s = A \times T^2 \times \exp(-W/kT);$$

wherein $j_s$ is the current density of the emission (mA/mm$^2$), A is Richardson's constant (approx. 1202 mA/mm$^2$K$^2$), T is the temperature of the emitter (K); W is the work function of the emitter (J), and k is the Boltzmann constant (1.38066E-23 J/K). According to the Richardson-Dushman equation, the work function of the metal emitter can be calculated by the values of the T and $j_s$, which can be measured directly. Apparently, a good thermionic emitter has to have a combination of properties including a low work function and a high operating temperature. However, metals with higher melting points typically have a higher work function, which is bad (i.e., not conducive) to the thermionic emission. As such, the thermionic emission method can usually be applied in measuring a work function of just a few kinds of metal, such as tungsten and so on. Still furthermore, the work function cannot be accurately measured when different kinds of metal emitters are measured in the thermionic emission method.

What is needed, therefore, is a method for measuring work function that has a relatively low operating temperature and that allows the work function of a plurality of metal materials to be measured accurately.

SUMMARY

In the preferred embodiment, a method for measuring work function includes the steps of: (a) providing a field emission electron source having a carbon nanotube tip as a cathode emitter and a spaced anode, the nanotube tip and the spaced anode having a predetermined spaced distance therebetween; (b) applying a voltage between the cathode and the anode and measuring a first current-voltage curve of the field emission electron source in a vacuum environment; (c) forming a layer of a field emission material whose work function is to be measured, the layer of the field emission material being formed at least on the surface of the carbon nanotube tip; (d) measuring a second current-voltage curve of the field emission electron source in the same predetermined spaced distance; (e) achieving two Fowler-Nordheim curves calculated from the two current-voltage curves according to the Fowler-Nordheim equation; and (f) comparing the two Fowler-Nordheim curves and further calculating the work function of the field emission material to be measured.

Other advantages and novel features of the present method for measuring work function will become more apparent from the following detailed description of preferred embodiments when taken in conjunction with the accompanying drawings.

BRIEF DESCRIPTION OF THE DRAWINGS

Many aspects of the present method for measuring work function can be better understood with reference to the following drawings. The components in the drawings are not necessarily to scale, the emphasis instead being placed upon clearly illustrating the principles of the present method for measuring work function.

Figure 1:
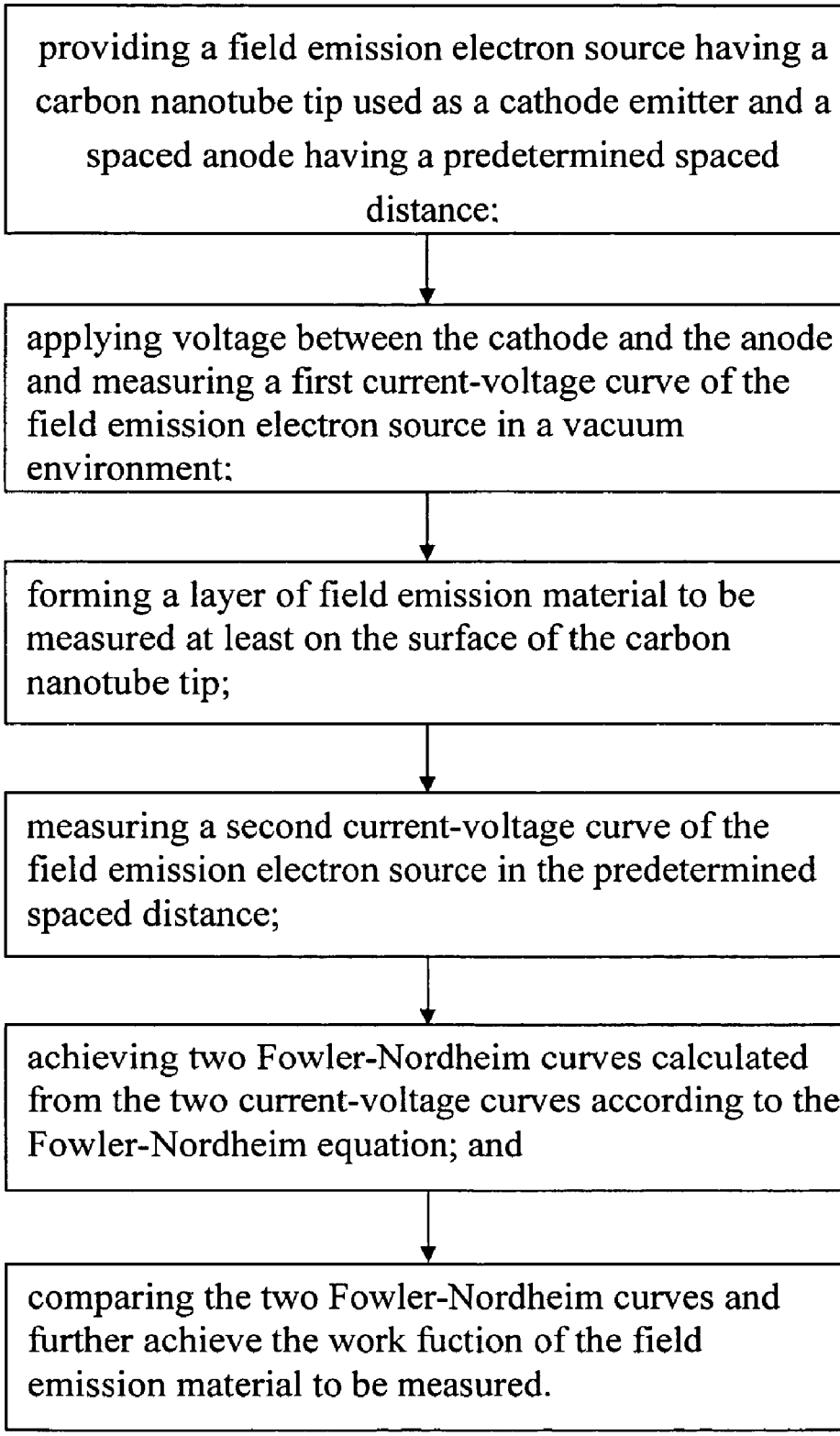
FIG. 1 is a flow chart showing a method for measuring work function of a field emission material, in accordance with an exemplary embodiment of the present method.

Corresponding reference characters indicate corresponding parts throughout the several views. The exemplifications set out herein illustrate at least one present method for measuring work function, in one form, and such exemplifications are not to be construed as limiting the scope of the invention in any manner.

DETAILED DESCRIPTION OF PREFERRED EMBODIMENTS

Reference will now be made to the drawings to describe embodiments of the present method for measuring work function, in detail.

Referring to FIG. 1, an embodiment of the present method for measuring work function is provided. The embodiment includes the following steps:

step (a), providing a field emission electron source having an uncoated carbon nanotube tip, used as a cathode emitter, and a spaced anode plate, the nanotube tip and the spaced anode having a predetermined spaced distance;

step (b), applying a voltage between the cathode and the anode and measuring a first current-voltage curve of the uncoated field emission electron source in a vacuum environment and at the predetermined spaced distance;

step (c), forming a layer of a field emission material at least on a surface of the carbon nanotube tip to form a coated field emission electron source, with the work function of the field emission material to be measured;

step (d), measuring a second current-voltage curve of the coated field emission electron source in the conditions same as that in step (b);

step (e), achieving two Fowler-Nordheim curves calculated from the two current-voltage curves according to the Fowler-Nordheim equation; and step (f), comparing the slopes of the two Fowler-Nordheim curves and further calculating the work function of the field emission material to be measured.

Figure 2:
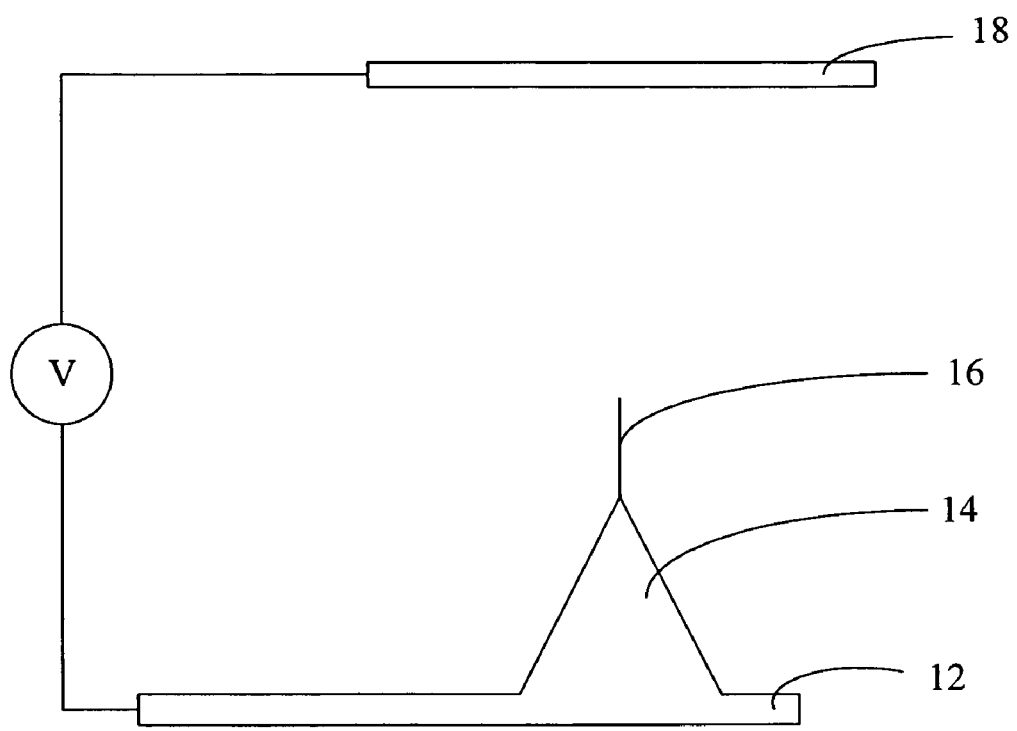
FIG. 2 is a schematic, side view of a device adapted for the method of FIG. 1, the device including a CNT-based field emission electron source.

In the step (a), as shown in FIG. 2, the field emission electron source 12, in accordance with a preferred embodiment of the present device adapted in the present method, includes a conductive base 14 having a tapered top and a carbon nanotube 16 formed on the tapered top. A connecting end of the carbon nanotube 16 is electrically connected with the tapered top of the conductive base 14. The connecting end is initially mechanically attached directly to the tapered top of conductive base 14 via van der Waals attractions therebetween. A free end of the carbon nanotube 16 has a tip extending outwardly away from the top of the conductive base 14 (i.e., essentially co-linear or at least essentially parallel with a center line of the conductive base 14). The free end of the carbon nanotube 16 is used as the cathode emitter of the field emission electron source 12. An anode plate 18 is disposed spaced apart from the free end of the carbon nanotube 16 with a predetermined distance. Preferably, the predetermined distance is about 500 μm and can be accurately controlled by an atomic force microscope to achieve the requirement of measuring expediency.

The conductive base 14 is advantageously made of a high-melting, oxidation resistant conductive material, preferably comprised of a metal selected from a group consisting of tungsten, gold, molybdenum, and platinum. Most preferably, due to the requirement of measuring expediency, the conductive base 14 is a probe of an atomic force microscope (AFM) with a film of gold formed thereon or is at least capable of being used as such a probe. The carbon nanotube 16 can be single-walled or multi-walled. Preferably, the carbon nanotube 16 is multi-walled. A diameter of the carbon nanotube 16 is approximately in the range from 1 to 50 nanometers, and a length thereof is about in the range from 10 to 100 micrometers.

The methods adopted for forming the carbon nanotube 16 on the conductive base 16 mainly include mechanical methods, the in-situ synthesis methods and electrophoretic methods. In the mechanical methods, a synthesized carbon nanotube is placed on a conductive base by an Atomic force microscope (AFM) and then fixed on the conductive base via a conductive paste or other adhesive. In the in-situ syntheses methods, metal catalysts are first coated on a conductive base and a carbon nanotube is synthesized on the conductive base directly by means of chemical vapor deposition (CVD). In the electrophoretic methods, a carbon nanotube is assembled on the conductive base by means of electrophoresis.

In the step (b), voltages are applied between the cathode conductive base 14 and the anode plate 18. The predetermined distance is maintained between the cathode conductive base 14 and the anode plate 18. Along with the increasing of the voltages, a plurality of electrons can overcome the work function barrier of the cathode emitter (i.e., the free end of the carbon nanotube 16) and escape outward from the surface of the cathode emitter and continually move to the anode plate 18. As a result, an electric current can be measured between the cathode conductive base 14 and anode plate 18, and a first current-voltage curve of the untreated/uncoated field emission electron source 12 is achieved by measuring the values of current and voltage between the cathode conductive base 14 and the anode plate 18.

In the step (c), the method of forming the field emission material to be measured further includes the steps as follows. Firstly, the surface of the carbon nanotube 16 is pretreated by forming a film of metal on at least the surface of the free end of the carbon nanotube 16. Advantageously, the film of metal is made of a material that has a relatively low work function, a high melting point, and, essentially, is readily coated on the surface of the carbon nanotube 16. Preferably, the film of metal is made of at least one material selected from a group consisting of titanium, zirconium, hafnium, niobium, and tantalum. The film of metal is formed on at least the free end of the carbon nanotube 16 by means, for example, of magnetron sputtering or electron beam evaporation. A thickness of the film of metal is in the approximate range from 1 to 10 nanometers. At a minimum, the film of metal needs to be formed on the free end of the carbon nanotube 14 in order to help promote electron emission therefrom. Preferably, the film of metal is formed on nearly the entire surface of the carbon nanotube and, yet more preferably, nearly the entire surface of the top of the corresponding conductive base 14 to which the carbon nanotube 16 is attached to, as well. Formed to this extent, the film of metal not only promotes an increase in the electron emission but also helps to bond the carbon nanotube 16 to the conductive base 14, thereby improving the electrical conductance and the mechanical connection therebetween. The film of metal beneficially is formed by means of magnetron sputtering and has a thickness of about 5 nanometers.

Secondly, the carbon nanotube 16 having the film of metal formed/coated thereon is further treated by applying an increased voltage to the now-treated/coated field emission electron source 12 in a vacuum environment, thereby causing the carbon nanotube 16 of the field emission electron source 12 to emit electrons. This emission ensures that the film of metal formed on the surface of the carbon nanotube 16 is carbonized by a chemical reaction and a layer of the field emission material, whose work function is to be measured, is formed. It is to be understood that the time of the emission needs to be controlled in the range from thirty minutes to two hours to make the film of metal be carbonized entirely and to avoid reducing the life of the carbon nanotube 16. Preferably, the time of the emission is thirty minutes, and a film of titanium carbide, zirconium carbide, hafnium carbide, niobium carbide, and/or tantalum carbide is formed on the surface of the carbon nanotube 16. This carbonizing process maintains a sufficient use of the geometrical characteristics (i.e., nearly a point source at the tip, with the layer of field emission material not adding significantly to the diameter thereof) of the carbon nanotube 16 needed for achieving good field emission. The thickness of the carbonized layer is approximately the same as that of the original metal film.

Alternatively, when the layer of field emission material to be measured is formed of lanthanum hexaboride or lanthanum, the layer is, as with the metal carbide versions, formed at least on the free end of the carbon nanotube by means of magnetron sputtering or electron beam evaporation, except that no subsequent carbonization step is required, which is a variance in the above-described step (c). Beyond that, the desired features (e.g., extent of the layer, deposition thickness, etc.) when lanthanum hexaboride or lanthanum are used for the layer of field emission material are generally the same as that when TiC and/or ZrC et al. are used for the layer of the field emission material.

It is to be understood that, in step (c), the field emission material to be measured by the present method may further be made of another conductive material. Basically, the field emission material must be capable of being readily coated on the surface of the carbon nanotube.

Figure 3:
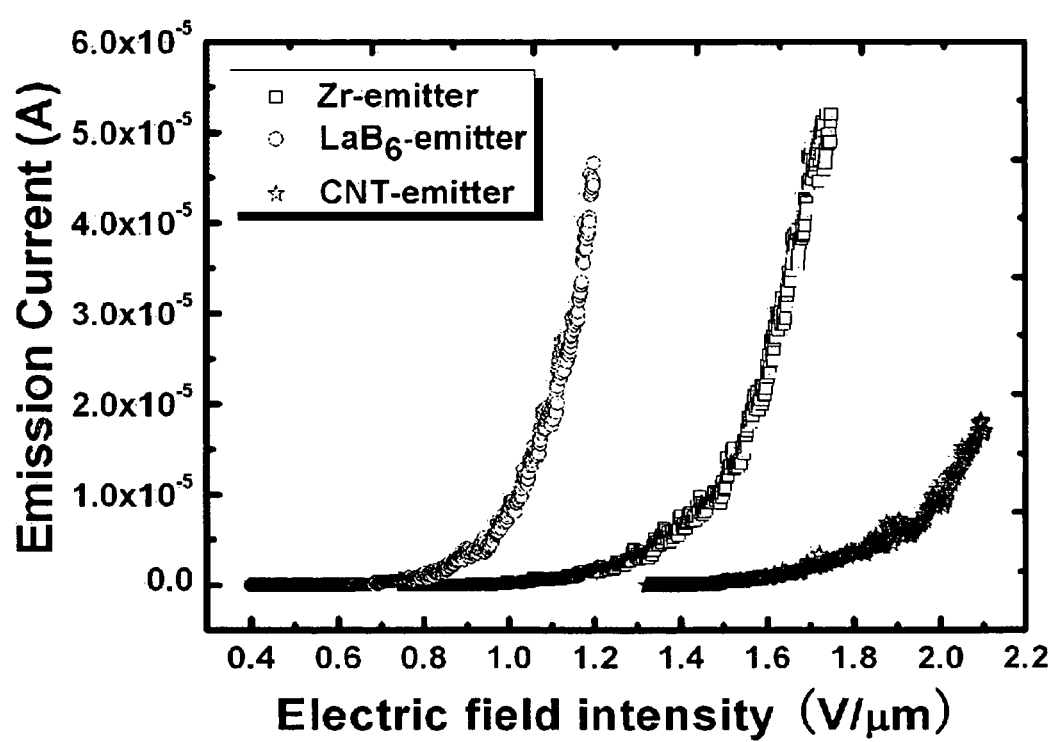
FIG. 3 is a series of current-voltage curves for CNT-based field emission electron sources, untreated and separately modified (i.e., coated) by different field emission materials to be measured.
Figure 4:
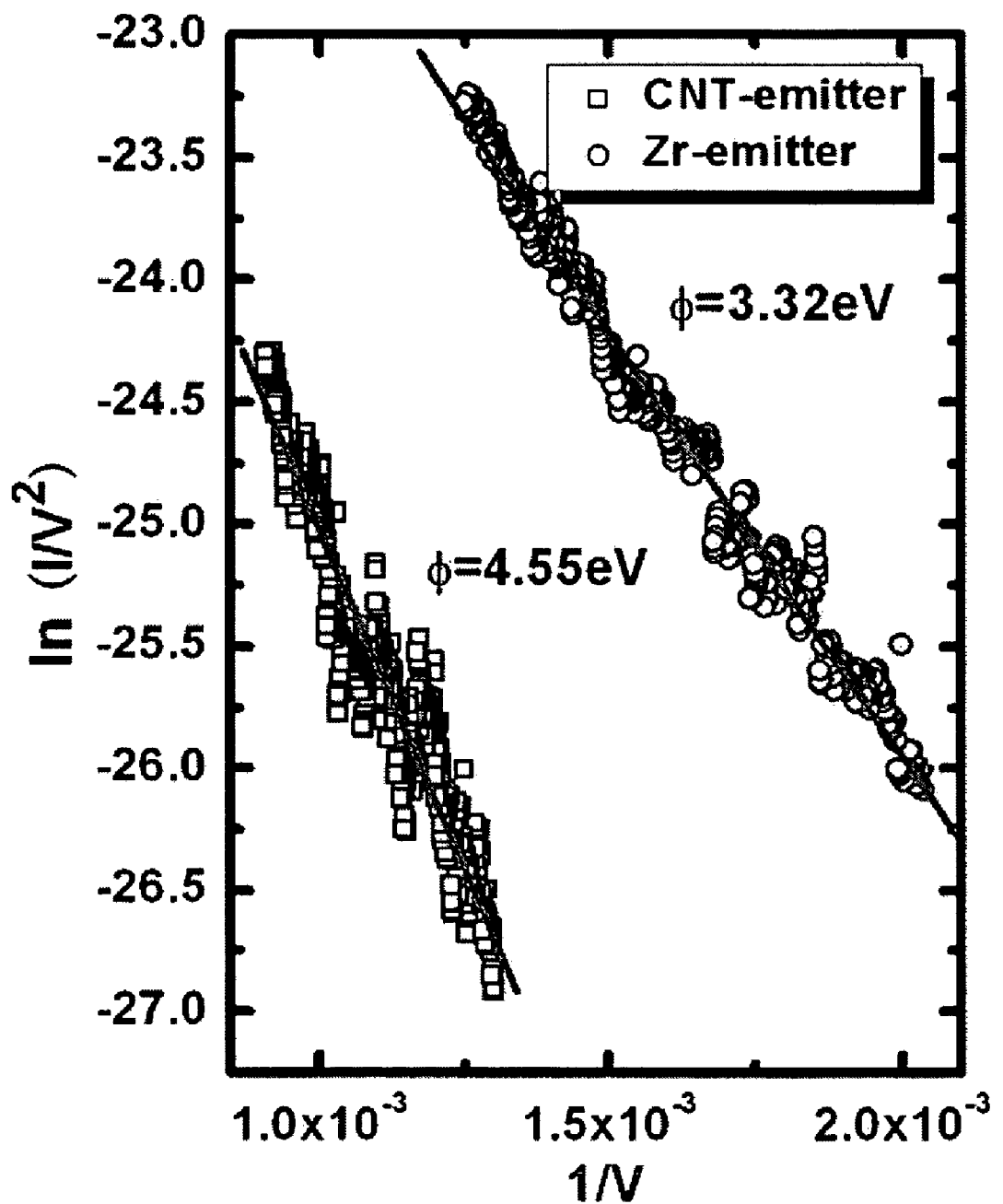
FIG. 4 is a series of Fowler-Nordheim curves for CNT-based field emission electron sources, untreated and modified by zirconium carbide.
Figure 5:
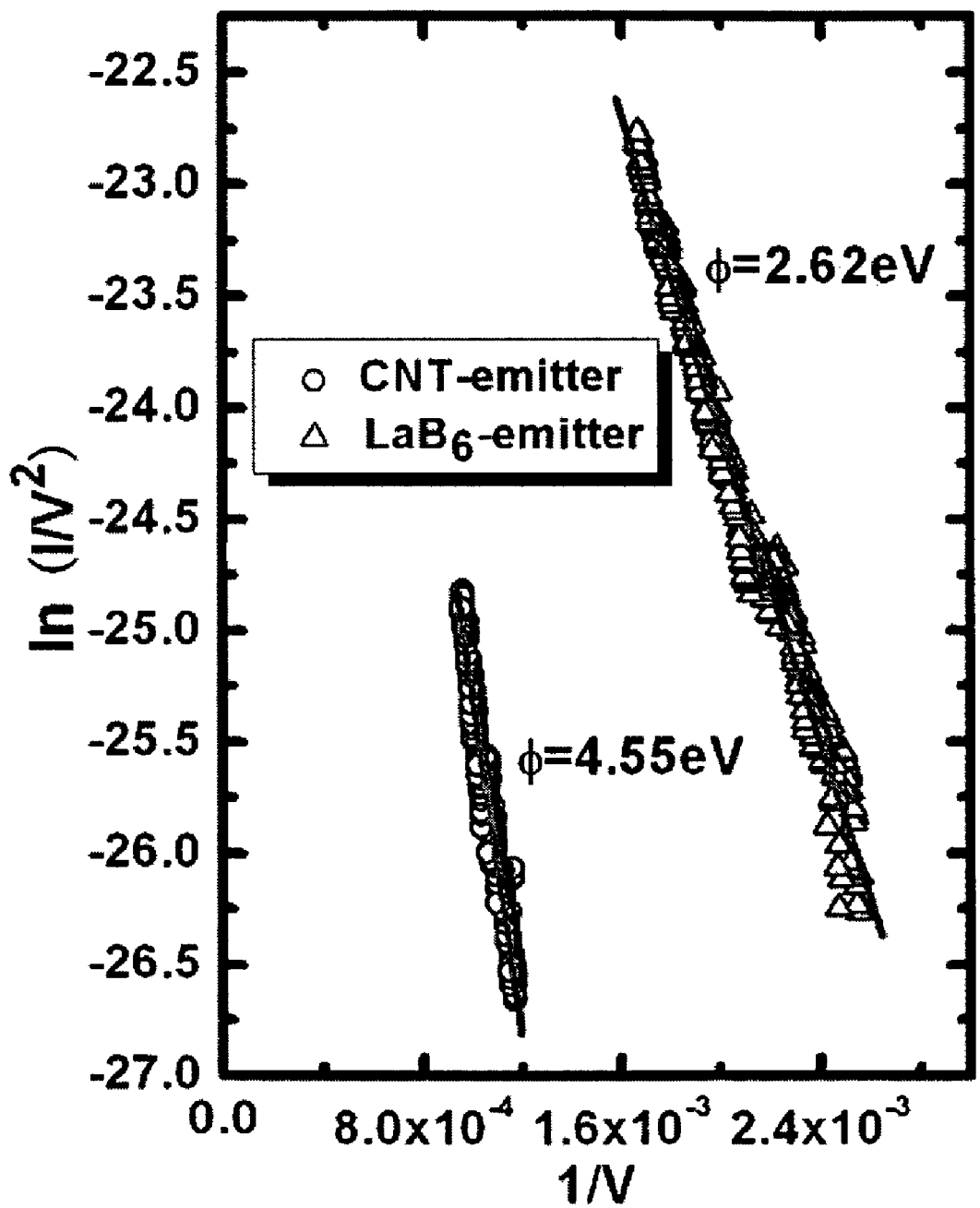
FIG. 5 is a series of Fowler-Nordheim curves for CNT-based field emission electron sources, untreated and modified by lanthanum hexaboride.

In step (d), a series of second current-voltage curves of field emission electron source 12 with the treated/coated carbon nanotube is measured in the conditions same as the measurement conditions for the first current-voltage curve of the untreated field emission electron source 12. Preferably, a series of second current-voltage curves of field emission electron source 12 is measured within the predetermined distance of 500 μm. Referring to FIG. 3, a series of current-voltage curves, untreated and separately treated by zirconium carbide and lanthanum hexaboride, for the present CNT-based field emission electron sources 12 are shown In step (e), the Fowler-Nordheim equation is shown as follows:

$$j_0 = \frac{1.54 \times 10^{-6} \varepsilon^2}{\phi} \exp\left[-\frac{6.83 \times 10^7 \phi^{3/2}}{\varepsilon} \theta\left(3.79 \times 10^{-4} \frac{\sqrt{\varepsilon}}{\phi}\right)\right];$$

wherein $j_0$ is the current of the emission, $\varepsilon$ is the electric field intensity of the emitter, and $\phi$ is the work function of the emitter. Further, $\varepsilon$ is satisfied by the equation of $\varepsilon=\beta V$, wherein $\beta$ is the field enhancement factor and is related to the geometrical structure of the emitter. In the preferred embodiment, the carbon nanotube 16 is used as the basis of the emitter of the field emission electron source 12. The geometrical structure of the emitter is unchanged after treated by different field emission materials. As such, $\beta$ is constant in the present method and a Fowler-Nordheims curve equation can be calculated from the Fowler-Nordheim equation. The Fowler-Nordheim curve equation is shown as follows:

$$\frac{d(\ln(I_1/V_1^2)/(1/V_1))}{d(\ln(I_2/V_2^2)/(1/V_2))} = \left(\frac{\phi_1}{\phi_2}\right)^{3/2};$$

wherein $I_1$, $V_1$ and $I_2$, $V_2$ are the values of currents and voltages measured in step (b) and step (d) separately, and $\phi_1$ and $\phi_2$ are the values of the work functions of the untreated and treated carbon nanotube emitter of the field emission electron source 12. Referring to the FIGS. 4 and 5, a series of Fowler-Nordheim curves, untreated and separately treated by zirconium carbide and lanthanum hexaboride, for the present CNT-based field emission electron sources 12 are shown. According to the Fowler-Nordheim curve equation, the value of the work function confirms the value of the slope of the Fowler-Nordheim curve. Therefore, the work function of the field emission material to be measured can be calculated from the Fowler-Nordheim curve equation because the work function of carbon nanotube is assured beforehand. As such, the work function of different field emission material can be measured by the present method. In the present embodiment, the work function of carbon nanotube is about 4.55 eV, the work function of the zirconium carbide and lanthanum hexaboride is about 3.32 eV and about 2.62 eV, separately.

It is also to be understood that the present method can further including repetitiously measuring the current-voltage curves of the field emission electron source treated by a same field emission material in different predetermined distances between the cathode conductive base 14 and the anode plate 18. As such, the work function of the field emission material to be measured can be measured most accurately.

Compared with conventional methods for measuring work function, the present method adopts forming the field emission material to be measured on the surface of the carbon nanotube emitter of the field emission electron source and achieving the work function the field emission material by measuring the current-voltage curves of an untreated/uncoated and a treated/coated carbon nanotube emitter in a vacuum environment. Firstly, the method of the preferred embodiment can exhibit the excellent field emission properties of the carbon nanotubes and achieve accurate value of the work function of the field emission material to be measured. Secondly, the present method can control different predetermined distances between the cathode conductive base and the anode plate by the AFM and measure the different current-voltage curves. Thirdly, the present method can measure a plurality of field emission material being readily coated on the surface of the carbon nanotube. Therefore, the manipulation of the present method is simple and well-suited for accurately measuring the work function of different materials.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

We claim:

1. A method for measuring work function, the method comprising the steps of:
   (a) providing an initially untreated field emission electron source having a carbon nanotube tip and a spaced anode, the carbon nanotube tip being used as a cathode emitter, the carbon nanotube tip and the spaced anode having a predetermined spaced distance therebetween;
   (b) applying a voltage between the cathode emitter and the anode and measuring a first current-voltage curve of the untreated field emission electron source in a vacuum environment and at the predetermined spaced distance;
   (c) forming a layer of a field emission material whose work function is to be measured, the layer of the field emission material being formed at least on the surface of the carbon nanotube tip to thereby result in a treated field emission electron source;
   (d) measuring a second current-voltage curve of the treated field emission electron source in the vacuum environment and at the predetermined spaced distance;
   (e) achieving two Fowler-Nordheim curves calculated from the two current-voltage curves according to the Fowler-Nordheim equation; and
   (f) comparing the two Fowler-Nordheim curves and further calculating the work function of the field emission material to be measured.

2. The method as claimed in claim 1, wherein in step (a), the carbon nanotube tip is formed by one of a mechanical method, an in-situ synthesis method, and an electrophoretic method.

3. The method as claimed in claim 1, wherein step (c) further comprises the steps of:
 (c1) forming a layer of a metal at least on the surface of the carbon nanotube tip; and
 (c2) carbonizing the layer of the metal to form the layer of field emission material thereon.

4. The method as claimed in claim 3, wherein the metal is comprised of a material selected from a group consisting of titanium, zirconium, hafnium, niobium and tantalum.

5. The method as claimed in claim 4, wherein the field emission material is comprised of a material selected from a group consisting of titanium carbide, zirconium carbide, hafnium carbide, niobium carbide and tantalum carbide.

6. The method as claimed in claim 3, wherein the layer of metal is formed by one of magnetron sputtering and electron beam evaporation.

7. The method as claimed in claim 1, wherein in step (c), the layer of the field emission material is formed on the surface of the carbon nanotube tip by a sputtering method.

8. The method as claimed in claim 1, wherein the field emission material is comprised of a material selected from a group consisting of lanthanum hexaboride and lanthanum.

9. The method as claimed in claim 1, wherein the predetermined spaced distance is about 500 μm.

10. The method as claimed in claim 1, wherein in step (e), a following Fowler-Nordheim curve equation is calculated from the Fowler-Nordheim equation:

$$\frac{d(\ln(I_1/V_1^2)/(1/V_1))}{d(\ln(I_2/V_2^2)/(1/V_2))} = \left(\frac{\phi_1}{\phi_2}\right)^{3/2};$$

wherein $I_1$, $V_1$ and $I_2$, $V_2$ are the values of current and voltage measured in step (b) and step (d) separately, and $\phi_1$ and $\phi_2$ are the values of the work functions of the carbon nanotube and the field emission material to be measured.

11. The method as claimed in claim 10, wherein $\phi_2$ is calculated from the Fowler-Nordheim curve equation.

* * * * *